United States Patent [19]

Rose et al.

[11] Patent Number: 4,738,846
[45] Date of Patent: Apr. 19, 1988

[54] VACCINE FOR VESICULAR STOMATITIS VIRUS

[75] Inventors: John K. Rose, Solana Beach, Calif.; Bernard Moss, Bethesda, Md.; Tilahun Yilma, Pullman, Wash.; Michael Mackett, Rusholme, England

[73] Assignee: The Salk Institute for Biological Studies, San Diego, Calif.

[21] Appl. No.: 645,998

[22] Filed: Aug. 30, 1984

[51] Int. Cl.[4] .................. A61K 39/12; C12N 1/00; C12N 15/00; C12N 7/00

[52] U.S. Cl. ......................... 424/87; 424/93; 435/70; 435/172.3; 435/320; 435/235; 935/12; 935/32; 935/57; 935/65

[58] Field of Search .............. 424/89, 93; 435/172.3, 435/68, 70, 172.1, 235-239, 240, 241, 317, 948; 935/32, 12, 57, 65

[56] References Cited

U.S. PATENT DOCUMENTS

| | | | |
|---|---|---|---|
| 4,237,224 | 12/1980 | Cohen | 435/172.3 |
| 4,419,446 | 12/1983 | Howley | 435/172.3 |
| 4,514,497 | 4/1985 | Kit | 435/235 |
| 4,556,556 | 12/1985 | Wiesehahn | 424/89 |
| 4,603,112 | 7/1986 | Paoletti | 435/235 |

OTHER PUBLICATIONS

Rose, J. K. et al, Journal of Virology, 39(2): 519-528 (8-1981).
Gallione, C. J. et al, Journal of Virology, 39(2): 529-535. (8-1981).
Panicalli, D. et al, Proc. Natl. Acad. Sci, USA, 79:4927-4931 (8-1982).
Rose, J. K. et al, Cell, 30:753-762 (10-1982).
Mackett, M. et al, Proc. Natl. Acad. Sci, USA, 79:7415-7419 (12-1982).
Sprague, J. et al, Journal of Virology, 45: 773-781 (2-1983).
Panicalli, D. et al, Proc. Natl. Acad. Sci. USA, 80:5364-5368 (9-1983).
Mackett, M. et al, Journal of Virology, 49(3):857-864 (3-1984).
Paoletti, E. et al, *Modern Approaches to Vaccines*, Cold Spring Harbor Laboratory, R. M. Chanock et al, eds (1984), pp. 295-299.
Mackett, M. et al, Ibid, pp. 301-305.
Smith, G. L. et al, Ibid, pp. 313-317.
G. L. Smith et al., *Nature (London)*, 302, 490 (1983).
C. J. Gallione et al., *J. Virol.*, 46, 162 (1983).

*Primary Examiner*—Margaret Moskowitz
*Attorney, Agent, or Firm*—Fitch, Even, Tabin & Flannery

[57] ABSTRACT

Synthetic vaccines for both the Indiana and New Jersey serotypes of vesicular stomatitis virus are provided. Recombinant vaccinia viruses are created with DNA sequences which encode antigenically active VSV proteins. Vaccinia virus sequences are inserted in plasmids and DNA sequences corresponding to encoding portions of the VSV genome are inserted into the plasmids with flanking vaccinia virus sequences. In cells transformed with such plasmids and also infected with vaccinia virus, homologous recombination occurs, producing the modified vaccinia viruses which act as vaccines encoding VSV proteins and inducing anti-VSV immune responses in inoculated animals.

6 Claims, 1 Drawing Sheet

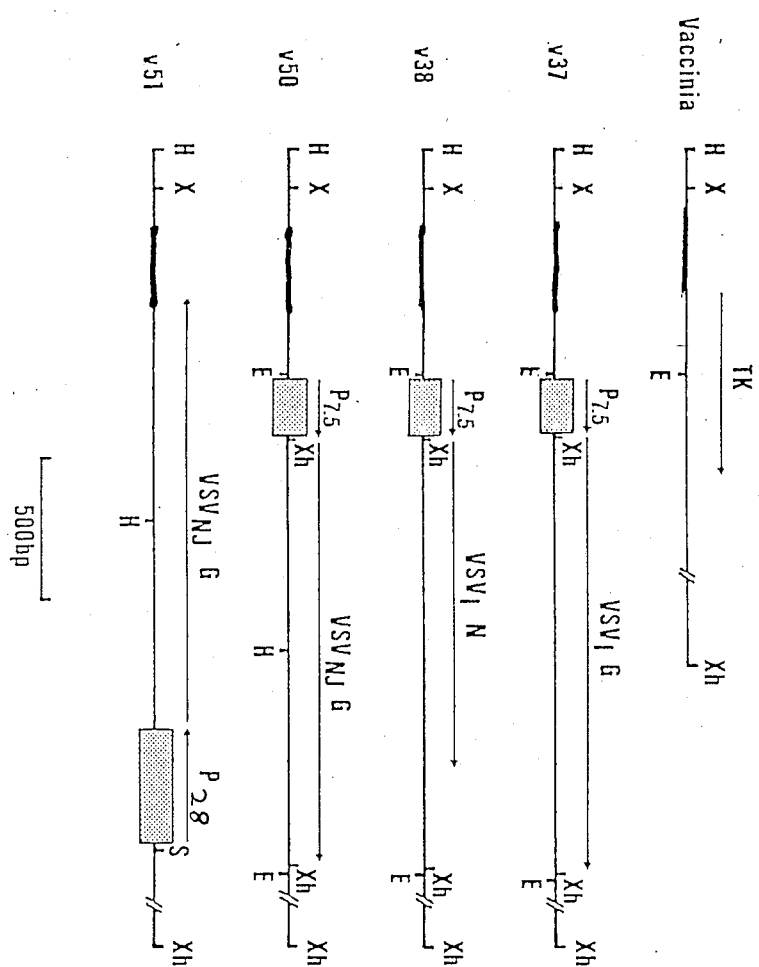

VACCINE FOR VESICULAR STOMATITIS VIRUS

The present invention was made in the course of work funded by the United States Goverment. The United States Goverment has certain rights in the invention.

The present invention relates to synthetic vaccines for vesicular stomatitis virus.

BACKGROUND OF THE INVENTION

Vesicular stomatitis virus (VSV), a member in the rhabdovirus family, causes a contagious disease in horses, cattle and pigs, characterized by lesions in the oral mucosa and udder. During the past few years, severe outbreaks of the disease in the United States, Mexico and parts of Central and South America produced substantial economic losses. There is also public health concern because humans can be infected, Patterson, W. C., et al., *J. Am. Vet. Med. Ass.*, 133, 57 (1958), and the virus may be spread by insect vectors, Ferris et al., *J. Infect. Dis.*, 96, 184 (1955), Tesh et al., *Science*, 175, 1477 (1972). Experimental attenuated and inactivated whole VSV vaccines provide some protection to animals; however, their use is usually not permitted by some governmental regulatory agencies, such as the United States Department of Agriculture, because of the inability to distinguish vaccinated animals from those naturally infected. Such a distinction could be made if subunit vaccines were developed. Moreover, subunit vaccines would eliminate the dangers associated with incomplete inactivation of VSV or the reversion of attenuated virus to virulence. However, whether use of subunit vaccines would be protective and economically feasible remains to be determined.

The approach taken in this invention to VSV immunization is to produce a synthetic vaccine in the form of a recombinant virus by inserting a nucleotide sequence corresponding to a segment of the VSV viral genome into a virus that is nonpathogenic to the vaccinated animal so that a VSV protein or protein segment is expressed by the recombinant virus. In particular, the invention inserts a DNA sequence corresponding to a segment of the VSV RNA genome into the vaccinia viral DNA genome, whereby the recombinant vaccine virus functions as a vaccine when innoculated into a VSV-susceptible animal.

The development of vaccinia virus as an infectious eukaryotic cloning vector (D. Panicali et al., *Proc. Natl. Acad. Sci. USA*, 79, 4927 (1982); M. Mackett et al., *Proc. Natl. Acad. Sci. USA*, 79, 7415 (1982); and M. Mackett et al., *J. Virol.*, 49, 857 (1984)) provides an alternative to whole virus or subunit vaccines. Heterologous genes, including hepatitis B virus surface antigen (G. L. Smith et al., *Nature (London)*, 302, 490 (1983); G. L. Smith et al., *UCLA Symposia on Molecular and Cellular Biol.*, New Series 8, 543 (1983); E. Paoletti et al., *Proc. Natl. Acad. Sci. USA*, 81, 193 (1984)), influenza virus hemagglutinin (D. Panicali et al., *Proc. Natl. Acad. Sci. USA*, 80, 5364 (1983), G. L. Smith et al., *Proc. Natl. Acad. Sci. USA*, 80, 7155 (1983)), herpes virus glycoprotein D (E. Paoletti et al., *Proc. Natl. Acad. Sci. USA*, 81, 193 (1984)), and malaria sporozoite surface antigen (G. L. Smith et al., *Science*, 224, 397 (1984)) have been expressed in this vector system. In several cases, vaccination has protected experimental animals against challenge with the corresponding pathogen. Perhaps because of the historical use of vaccinia virus as a smallpox vaccine, attention has focused on human applications. However, the presumed origin of vaccinia virus from cowpox and its ability to infect a variety of domesticated animals raises the possibility of veterinary uses as well.

VSV contains a single negative strand of RNA which encodes 5 known proteins. Two VSV serotypes, Indiana ($VSV_I$) and New Jersey ($VSV_{NJ}$), are known. Although the diseases caused by the two VSV serotypes are similar, they are immunologically distinct and are found in separate enzootic areas within the Western Hemisphere. Complementary DNA copies of mRNA for the G, M, N, and NS proteins of $VSV_I$ have been cloned and sequenced (J. K. Rose et al., *J. Virol.*, 39, 519 (1981); C. J. Gallione et al., *J. Virol.*, 39, 529 (1981); C. J. Gallione et al., *J. Virol.*, 46, 162 (1983). The G and N genes of the Indiana serotype have been expressed in eukaryotic cells (J. K. Rose et al., *Cell*, 30, 753 (1982); J. Sprague et al., *J. Virol.*, 45, 773 (1983)). The sequence of the $VSV_{NJ}$ virus is reported in Gallione, C. J. and Rose, J. K., *Journal of Virology* 46, 162–169 (1983). This article also reports the isolation of $VSV_{NJ}$ cDNA, including that corresponding to the genome segment which encodes the G protein.

IN THE DRAWING

The FIGURE represents chimeric VSV genes in vaccinia virus recombinants.

SUMMARY OF THE INVENTION

Vaccinia virus DNA segments are translocated to plasmid vectors. cDNA corresponding to protein-encoding portions of the VSV genome are modified for insertion into the translocated vaccinia virus segments of the recombinant plasmids and are inserted so that vaccinia virus sequences flank the VSV sequences. Cells are transformed with the recombinant plasmids, which contain VSV sequences flanked by vaccinia virus sequences, and are also infected with vaccinia virus. Homologous recombination occurs within the cell, thereby introducing the vaccinia virus sequences with the flanked VSV sequences into the complete vaccinia virus genome. Recombinants are selected, e.g., by means which select for destruction of a vaccinia virus protein function. Selected recombinant vaccinia viruses are shown to induce immunity to VSV in mice inoculated therewith and to raise significant antibody titers in cattle inoculated therewith.

DETAILED DESCRIPTION OF THE INVENTION

In accordance with the invention, recombinant viruses are constructed which contain nucleotide sequences corresponding to sequences of the VSV viral genome and which, when inoculated into a VSV-suceptable animal, induce an immune response. Immune responses have been shown to afford protection to subsequent exposure to virulent VSV virus.

Briefly, to produce the recombinant viruses, segments of the vaccinia virus are inserted into plasmids. cDNA is produced from VSV mRNA copied from the RNA viral genome and is inserted in the plasmid under the control of a vaccinia viral promoter sequence and flanked by vaccinia viral sequences. Cells are infected with vaccinia virus, and the infected cells are transformed with the recombinant plasmids. Homologous recombinations of plasmid DNA and vaccinia virus DNA result in vaccinia viruses which incorporate the VSV sequences. Because insertion of the VSV sequence into the vaccinia virus sequence frequently destroys or truncates a vaccinia virus protein, thereby altering a vaccinia viral function, recombinant vaccinia viruses are selectable from the wild type on the basis of this altered function. Recombinant vaccinia virus can be inoculated into an animal wherein it produces a mild, localized infection. Animals so inoculated have been shown to produce high titers of anti-VSV antibody and have been shown to be resistant to virulent VSV in dosages which ordinarily would result in almost certain death of the VSV-exposed animal. Recombinant vaccinia viruses containing sequences of both VSV serotypes, $VSV_I$ and $VSV_{NJ}$, have been constructed.

The invention will now be described in greater detail by way of specific examples.

EXAMPLE 1

The strategy for using vaccinia virus as a vector involves the formation of chimeric genes containing a translocated vaccinia virus promoter region linked to the coding segment of a foreign gene. The chimeric gene is then incorporated into the vaccinia virus genome by homologous recombination in cells that have been transfected with a plasmid and infected with vaccinia virus. Although any nonessential region of the vaccinia virus genome can be used as the site of insertion, the thymidine kinase (TK) locus provides some advantages and was therefore used. The TK⁻ phenotype of such recombinants distinguish them from wild type TK⁺ virus. This phenotype provides a simple method of selection (M. Mackett et al., *Proc. Natl. Acad. Sci. USA*, 79, 7415 (1982)), and also serves to attenuate viral pathogenicity. Entire coding sequences of the cloned $VSV_I$ and $VSV_{NJ}$ genes, described above, can be excised from recombinant plasmids with restriction endonuclease XhoI.

To facilitate the cloning of XhoI-cut DNA fragments into vaccinia virus, a previously used plasmid vector, pGS20 (M. Mackett et al., *J. Virol.*, 49, 857 (1984)), was modified to contain a unique XhoI site downstream of a promoter and a RNA start site translocated from a vaccinia virus gene encoding a 7.5kD protein. The plasmid designated pMM34 was constructed by cleaving pGS20 with XhoI and partially digesting with AvaI. A DNA fragment of approximately 5 kb was isolated. The ends of the latter were ligated together and used to transform *E. coli* HB101. A resulting plasmid lacking an XhoI site was designated pMM30. The latter was cleaved with SmaI and ligated to a phosphorylated XhoI linker to form pMM31. This plasmid was then cleaved with HindIII and partially digested with PvuII. The 5' overhanging end of the HindIII site was filled in with DNA polymerase I large fragment, and a 4.2 kb DNA segment was isolated. The ends of the DNA were ligated together, resulting in the plasmid designated pMM34.

Into the pMM34 plasmid was placed the G or N genes from $VSV_I$ so that the vaccinia virus transcriptional and VSV translational start sites were juxtaposed, and the resulting chimeric gene was flanked by segments of the vaccinia virus TK gene.

The G protein gene from $VSV_{NJ}$ was modified so that it also could be inserted into the XhoI site of pMM34 as well as into the unique SalI site of another plasmid vector, pLTP1, which contains the promoter region of a vaccinia virus gene encoding a protein of 28kD. The promoter regions of the 7.5kD and 28kD protein genes operate under different regulatory control mechanisms.

The G protein gene from $VSV_{NJ}$, described in C. J. Gallione et al. (1983) supra., was modified as follows. To obtain a G gene suitable for insertion into the expression vector, the insert from pNJG6 was first excised by partial digestion with PstI. The full length insert (uncut at the internal PstI site) was purified by polyacrylamide gel electrophoresis and trimmed with nuclease Ba131 to remove the G:C tails which had been added during the initial cloning. Synthetic DNA linkers containing the XhoI site (CCTCGAGG) were then ligated to the trimmed DNA (the procedures for Ba131 digestion and linker addition were as described by Rose and Shafferman, PNAS 78: 6670–6674, 1981). This DNA was then cloned into the single XhoI site of plasmid JC119, (J. Sprague et al., *J. Virol.*, 45, 773 (1983)). One plasmid obtained by this procedure (designated pNJGE-2) was found to have the sequence GGTATG ... at the 5' end following the XhoI linker. The ATG is the initiation codon for the $VSV_{NJ}$ G protein.

The FIGURE represents chimeric VSV genes in vaccinia virus recombinants. A 2,000 base pair segment from the left side of the HindIII J fragment of vaccinia virus (G. Bajszar et al., *J. Virol.*, 45, 62, (1983); J. P. Weir et al., *J. Virol.*, 46, 530 (1983)) is shown on the top line. The four lower lines contain chimeric VSV genes inserted into the body of the TK gene. Recombinants v37, v38, v50 were constructed by insertion of the indicated VSV gene into the unique XhoI site of pMM34; v51 was constructed by inserting the $VSV_{NJ}$ G gene into the unique SalI site of pLTP1. The promoter regions of vaccinia virus genes encoding polypeptides of 7.5kD and 28kD are indicated as P7.5 and P28. Abbreviations for restriction endonuclease are H, HindIII; B, BamHI; E, EcoRI; S, SmaI; X, XbaI; Xh, XhoI.

The recombinant vaccinia viruses diagrammed in the FIGURE were infected into tk⁻143 cells, and the plasmids were transfected into the vaccinia virus-infected cells by the method of Weir, J. P. et al., *Proc. Natl. Acad. Sci. USA*, 79, 4927–4931 (1982). Homologous recombinations between the plasmid constructs and vaccinia viral DNA produced the recombinant vaccinia viruses carrying the VSV sequences.

Recombinant virus was selected in TK⁻143 cells in the presence of 5-bromodeoxyuridine (BudR). Individual virus plaques were picked and used to infect 2 cm² monolayers under the selective conditions of M. Mackett et al., *Proc. Natl. Acad. Sci. USA*, 79, 7415 (1982). The presence of recombinant virus was confirmed by hybridization of a ³²P-labeled VSV DNA probe (M. Mackett et al., *Proc. Natl. Acad. Sci. USA*, 79, 7415 (1982)) and/or by binding of VSV antibodies and ¹²⁵I-staphylococcal A protein to lysate material immobilized on nitrocellulose. For the $VSV_{NJ}$ G protein gene recombinants, both procedures were used, and in one case, 18 out of 24 TK⁻ plaques were positive by both assay procedures, and in another case, 10 out of 24 were positive. Recombinant viruses were purified by at least 2 plaque assays in the presence of BudR, and then virus stocks were prepared without selection in HeLa S-3 cells. Correct insertion of the chimeric genes was verified by digestion of genomic DNA extracted from purified virus with at least 2 appropriate restriction endonucleases, followed by agarose gel electrophoresis, transfer to nitrocellulose and hybridization to ³²P-labeled VSV and vaccinia virus DNA probes.

Evidence for expression of the VSV genes and an indication of the purity and stability of the recombinant viruses was obtained by binding antibody directly to virus plaques. Antiserum to $VSV_I$ or $VSV_{NJ}$ was incubated with fixed monolayers containing plaques of recombinant or wild-type virus and binding IgG was detected with $^{125}I$-staphylococcal A protein followed by autoradiography. Direct comparisons of stained cell monolayers and x-ray film indicated that all v50 and v51 plaques bound antibody raised against $VSV_{NJ}$. In contrast, VSV antibody did not bind to plaques of wild-type vaccinia virus. As expected, all plaques bound antibody to vaccinia virus. Similar results were obtained when v37 and v38 plaques were incubated with the appropriate $VSV_I$ or $VSV_{NJ}$ antibody.

Cells infected with recombinants v37, v38, v50 and v51 were pulse-labeled with $^{35}S$-methionine, and the polypeptides immunoprecipitated by anti-VSV sera were dissociated with sodium dodecyl sulfate and resolved by polyacrylamide gel electrophoresis. Fluorographs revealed that v50 and v51 synthesized similar amounts of a specifically immunoprecipitable polypeptide of approximately 65kD that co-migrated with G protein produced in cells infected with $VSV_{NJ}$. Similarly, v37 and v38 expressed immunoprecipitable polypeptides of approximately 67kD and 45kD that co-migrated with authentic $VSV_I$ G and N proteins, respectively. The correct sizes of the G proteins produced by the recombinants suggests that the extent of glycosylation is similar to that occurring in cells infected with VSV.

In cells infected with VSV, the G protein is transported through the Golgi apparatus to the cell surface. Double-label immunofluorescence of cells infected with recombinant vaccinia viruses v50 and v51 showed clear cell surface labeling of the $VSV_{NJ}$ G protein. Internal labeling of the same cells showed strong fluoroscence of the Golgi region, which is typical of normal G protein (J. K. Rose et al., Cell 30, 3 (1982)). Virtually all cells were infected with v50 or v51 and showed similar levels of staining. In contrast, there was no surface staining of cells infected with wild-type vaccinia virus, although there was faint, nonspecific staining within permeabilized cells.

A rapid antibody binding procedure was used to investigate the regulation of synthesis of the $VSV_{NJ}$ G protein made in cells infected with v50 and v51. Cells were harvested at 2, 6, or 12 hours after infection with recombinant or wild-type vaccinia virus. Serial two-fold dilutions of the extracts were spotted onto a nitrocellulose filter which was then incubated successively with $VSV_{NJ}$ antisera and $^{125}I$-labeled staphylococcal A protein. In this procedure, washed cells were lysed in 0.1 M Tris-HCl (pH 8.0), 0.1 M NaCl, 0.5% Nonidet P-40 detergent and 0.1% Aprotinin. Nuclei were removed by centrifugation, and the cytoplasm was diluted with lysis buffer and 20 ul samples were applied to nitrocellulose. After air drying, the dot blot was incubated with rocking for 2 hours with 4% bovine serum albumin, 0.2% sodium azide. Antiserum was added, and the incubation was continued for an additional 2 hours. The dot blot was then washed 5 times with phosphate buffered saline and incubated with rocking for 2 hours with 4% albumin, 0.02% sodium azide, and 1 uCi of $^{125}I$-staphylococcal A protein. After 5 washes with phosphate buffered saline, the dot blot was exposed to X-ray film. Examination of autoradiographs indicated that, in cells infected with v50, G protein was made within 2 hours and was abundant by 6 hours.

In contrast, G protein synthesis was first detected at 6 hours after infection with v51. These results are consistent with previous data that indicated that the promoter of the 7.5kD gene (used for v50) is active at both early and late times after infection (M. Mackett et al., J. Virol., 49, 857 (1984)), whereas the promoter for the 28kD protein gene (used for v51) is active only at late times (J. P. Weir et al., J. Virol., 55,662 (1984)). The effect of cytosine arabinoside, an inhibitor of DNA replication, on expression of G protein in cells infected with v51 provides further evidence that the fidelity of regulation of these chimeric genes is maintained.

EXAMPLE 2

Because the New Jersey strain has been responsible for the recent VSV outbreaks in the western United States, the animal studies described here were carried out with $VSV_{NJ}$ sequence-containing vaccinia virus. To protectively immunize against VSV infection, the appropriate VSV gene must be expressed during replication of the recombinant vaccinia virus in the inoculated animal. Of the 5 known proteins of VSV, only antibody to the G protein has been shown to be protective in experiments carried out with mice (B. Dietzschold et al., J. Virol., 14, 1 (1974)). After mice were injected with $10^5$ PFU of purified infectious v50 intradermally in the caudal fold of the tail, significant VSV neutralization titers were detected by day 14 and increased over a 42 day period (Table 1 below). About half of the mice were given a booster vaccination on day 28 which resulted in a 7 to 8-fold increase in serum VSV neutralization titers.

The VSV challenge was carried out by injecting approximately $10^8$ PFU of $VSV_{NJ}$, isolated from the vesicular fluid of an infected cow, into the tail vein of each mouse. This produces an acute encephalitis that causes death in 6 to 12 days. For control purposes, one group of mice had been vaccinated 44 days earlier with vHBs4 (G. L. Smith et al., Nature (London), 302, 490 (1983)), a vaccinia virus recombinant that contains the hepatitis B virus surface antigen gene rather than of $VSV_{NJ}$ G protein gene. When this control group was challenged, 7 out of 11 animals died of encephalitis. By contrast, only 1 out of 15 mice that received a primary vaccination with v50 died, and none out of 16 that received 2 vaccinations died. The results are summarized in Table 1.

TABLE 1

| Average Serum Neutralization Titers of Vaccinated Mice and Response to Challenge with $VSV_{NJ}$ | | | | | | |
|---|---|---|---|---|---|---|
| Group | Day 6 | Day 14 | Day 28 | Day 42 | No. Mice Challenged | No. Mice Died |
| vHBs4 | 0 | 0 | 0 | 0 | 11 | 7 |
| v50 | 10 | 20 | 420 | 760 | 15 | 1 |
| v50(2x) | | | | 5220 | 16 | 0 |

Mice were vaccinated intradermally With $10^5$ PFU of purified vHBs4 or v50 at a single site in the caudal fold of the tail. All mice recieved a primary vaccination on day 0, and half (designated 2x) received a booster vaccination on day 28. Serum neutralization titers are expressed as the reciprocal of the dilution of serum that gave complete protection against the cytopathic effect of 100 tissue cultures infectious dose$_{50}$ units of $VSV_{NJ}$. Mice were challenged 44 days after the primary vaccination with $10^8$ PFU of $VSV_{NJ}$ by intravenous administration in the tail vein.

EXAMPLE 3

Cattle vaccinated intradermally with either v50 or vHBs4 developed typical pox lesions in four days. The lesions were confined to the sites of inoculation and were characterized by the formation of papules which gradually changed to pustules with a small umbilication. Two weeks post-vaccination, the lesions dried up and were covered by dry scabs which eventually fell off leaving unscarred surfaces. In cattle vaccinated with v50, VSV neutralization titers were significant on day 7 and reached values of 80 to 480 by day 28. At that time, a second vaccination was given following which the titers increased several-fold. On day 44, the cattle were challenged by injection of $10^2$ and $10^3$ PFU of $VSV_{NJ}$ into the 2 upper and 2 lower quadrants of the tongue, respectively. Preliminary experiments indicated that unvaccinated cattle, challenged in this manner, develop vesicular lesions within 1 day. Both cows (23Y and 26Y) vaccinated with the recombinant expressing the hepatitis B virus surface antigen and 2 cows vaccinated with v50 developed typical vesicular lesions at the $10^2$ PFU and $10^3$ PFU VSV injection sites (Table 2). The remaining 4 cows (24Y, 27Y, 28Y, and 29Y) that were vaccinated with v50 had no lesions at the $10^2$ PFU VSV injection sites although they all developed lesions at the $10^3$ PFU sites. In one case (cow 28Y), the VSV lesion at the $10^3$ PFU site remained localized, whereas in all others it generalized to the remaining surface of the tongue. The results are summarized in Table 2.

nation is quite important. Boosting of antibodies to $VSV_{NJ}$ G glycoprotein only 28 days after primary vaccination of mice and cattle was demonstrated. In other experiments, boosting of antibodies to influenza virus hemagglutinin and hepatitis B virus surface antigen occurred after secondary vaccination of rabbits. Evidently, sufficient replication of recombinant vaccinia virus permits antigen production even in the presence of neutralizing antibodies to vaccinia virus.

Previous experience with smallpox vaccine suggests that there would be numerous advantages to the development of vaccinia virus or other poxvirus recombinants as veterinary vaccines. Vaccinia virus can be economically grown in the skin of cattle or in tissue culture and stored in a heat-resistant lyophilized form. The ability of recombinant vaccinia virus to stimulate a cytotoxic T cell response specific for a foreign surface glycoprotein is believed to represent a significant advantage over subunit or inactivated whole vaccines, which in general do not prime effectively for cell-mediated immunity. The large capacity of vaccinia virus for foreign DNA (G. L. Smith et al., Gene 25, 21 (1983)) also raises the possibility of multivalent vaccines for different serotypes of the same virus or even against entirely different pathogenic agents.

A sample of the recombinant vaccinia virus herein

TABLE 2

| Cow Number | Serum Neutralization Titers of Vaccinated Cattle and Response to Challenge with $VSV_{NJ}$ | | | | | | | | |
|---|---|---|---|---|---|---|---|---|---|
| | Vaccine | Pre-challenge Titers | | | | | | Vesicular Lesion | |
| | | Day 0 | Day 7 | Day 14 | Day 21 | Day 28 | Day 35 | Day 44 | $10^2$ PFU | $10^3$ PFU |
| ? | none | — | — | — | — | — | — | — | + | + |
| ? | none | — | — | — | — | — | — | — | + | + |
| 23y | vHBs4 | 0 | 0 | 0 | 0 | 0 | 0 | 0 | + | + |
| 26y | vHBs4 | 0 | 0 | 0 | 0 | 0 | 5 | 30 | + | + |
| 17y | v50 | 0 | 10 | 120 | 120 | 160 | 320 | 640 | + | + |
| 24y | v50 | 0 | 160 | 480 | 480 | 320 | 960 | 2560 | — | + |
| 25y | v50 | 0 | 30 | 160 | 240 | 80 | 320 | 480 | + | — |
| 27y | v50 | 0 | 80 | 80 | 80 | 80 | 960 | 1920 | — | + |
| 28y | v50 | 0 | 80 | 160 | 240 | 320 | 640 | 1280 | — | + |
| 29y | v50 | 0 | 160 | 160 | 160 | 160 | 1280 | 2560 | — | + |

Cows were vaccinated intradermally with $4 \times 10^8$ PFU of purified vHSs4 or v50 at four sites on Day 0 and Day 28. They were then challenged 44 days after the primary vaccination by intradermal inoculation of $10^2$ and $10^3$ PFU of $VSV_{NJ}$ on the two upper and two lower quadrants of the tongue, respectively. Serum neutralization titers are expressed as the reciprocal of the dilution of serum that gave complete protection against cytopathic effect of 100 $TCID_{50}$ of $VSV_{NJ}$.

A striking correlation was observed between antibody titers and protection to challenge with $10^2$ PFU of VSV. All animals with neutralizing antibody titers of 1280 or greater were protected, whereas those with titers of 640 or lower were sensitive.

The ecology and method of transmission of $VSV_{NJ}$ to domesticated animals is not well understood and may involve insect vectors. For this reason, the design of animal models is difficult, and it is likely that the challenge used in the examples was more severe than that occurring naturally. Ordinarily, the incubation period is from 2 to 4 days, whereas after direct injection of VSV into the tongue, vesicles were seen within 1 day. Nevertheless, two successive vaccinations provided protection for two-thirds of the animals inoculated with 100 PFU of VSV. Protection was closely correlated with neutralizing antibody titers, although other factors including cell-mediated immunity may be involved in protection. Because the engineering of vaccinia virus vectors for high expression is just beginning, it can reasonably be expected that recombinants synthesizing considerably more G glycoprotein will be available in the future.

Because the duration of immunity is not yet known, the ability to boost antibody levels by secondary vaccidesigned v50 has been deposited with the American Type Culture Collection (ATCC) at 12301 Parklawn Drive, Rockville, MD 20852 USA and has been given the ATCC accession number VR-2094. A sample of the recombinant vaccinia virus herein designated v37 has also been deposited and has been assigned the ATCC accession number VR-2095.

While the invention has been described in terms of certain preferred embodiments, modifications obvious to one with ordinary skill in the art may be made without departing from the scope of the present invention. While the invention has been described particularly with respect to insertion of VSV segments into vaccinia virus, VSV segments may be inserted into other suitable carrier viruses, including, but not limited, to other pox viruses. To be suitable as a carrier, a virus must be capable of carrying a nucleotide sequence of sufficient length to encode either an entire antigenically active VSV protein or an antigenically active portion thereof.

While the method of producing the vaccine has been described with reference to forming recombinant plasmids which undergo homologous recombinations with the carrier, e.g., vaccinia, virus, other cloning vectors, such as other viruses and cosmids, might serve this purpose equally as well.

Very importantly, the carrier virus must be generally nonpathogenic to the animal which is to be inoculated. By generally nonpathogenic, it is meant that the carrier virus should cause no serious infection; however, it is acceptable that the carrier virus induce a localized infection, such as the localized pox associated with small pox vaccine.

Each of the vaccinia viruses constructed herein carries the entire protein-encoding sequence; however, a sequence that encodes a truncated, but antigenically active, protein may be sufficient to induce the desired immune response.

Various features of the invention are set forth in the following claims.

What is claimed is:

1. A synthetic vaccine, for immunizing a mammal against VSV, which comprises a recombinant vaccinia virus, the genome of which comprises, in a non-essential region, a DNA segment which, in cells of a mammal infected by said virus, is transcribed under control of a vaccinia virus promoter into an RNA which is translated into the G protein of a VSV of Indiana serotype or New Jersey serotype.

2. A vaccine according to claim 1 wherein the RNA, which is translated into a VSV G protein, is translated into a G protein of a VSV of New Jersey serotype.

3. A vaccine according to claim 1 wherein the RNA, which is translated into a VSV G protein, is translated into a G protein of a VSV of Indiana serotype.

4. A vaccine according to claim 2 wherein the recombinant vaccinia virus is v50.

5. A vaccine according to claim 2 wherein the recombinant vaccinia virus is v51.

6. A vaccine according to claim 3 wherein the recombinant vaccinia virus is v37.

* * * * *